United States Patent [19]

Matsumura et al.

[11] Patent Number: 5,367,144
[45] Date of Patent: Nov. 22, 1994

[54] AIR PERMEABILITY DETECTING METHOD AND APPARATUS FOR THE SAME

[75] Inventors: Takeshi Matsumura; Mikio Komori, both of Tokyo, Japan

[73] Assignee: Japan Tobacco Inc., Tokyo, Japan

[21] Appl. No.: 136,924

[22] Filed: Oct. 18, 1993

[30] Foreign Application Priority Data

Oct. 20, 1992 [JP] Japan .................. 4-281456

[51] Int. Cl.$^5$ .............................................. B23K 26/00
[52] U.S. Cl. ....................... 219/121.84; 219/121.7; 219/121.71; 219/121.83
[58] Field of Search .......... 219/121.7, 121.71, 121.83, 219/121.84; 131/281

[56] References Cited

U.S. PATENT DOCUMENTS

| | | | |
|---|---|---|---|
| 4,297,559 | 10/1981 | Whitman, III | 219/121.7 X |
| 4,500,770 | 2/1985 | Vock et al. | 219/121.7 |
| 4,767,909 | 8/1993 | Okumoto | 219/121.7 |
| 4,916,272 | 4/1990 | Okumoto et al. | 219/121.7 |
| 5,117,087 | 5/1992 | Baker et al. | 219/121.71 |
| 5,179,965 | 1/1993 | Komori et al. | 131/281 |
| 5,186,183 | 2/1993 | Komori et al. | 131/281 |
| 5,210,390 | 5/1993 | Okumoto | 219/121.7 |

FOREIGN PATENT DOCUMENTS 2-18677 4/1990 Japan .

*Primary Examiner*—C. L. Albritton

[57] ABSTRACT

In a method of controlling the air permeability of the hole portion of chip paper in which holes are formed by a laser, the flow rate of permeating air from an air permeable portion of a dummy prepared in advance and the flow rate of permeating air from the hole portion are respectively converted to pressures. An output from the laser is controlled such that the pressure difference between the two pressures becomes zero. Then, an influence caused by variations in suction pressure can be prevented. Accordingly, the air permeability can be detected without being influenced by variations in suction pressure.

7 Claims, 3 Drawing Sheets

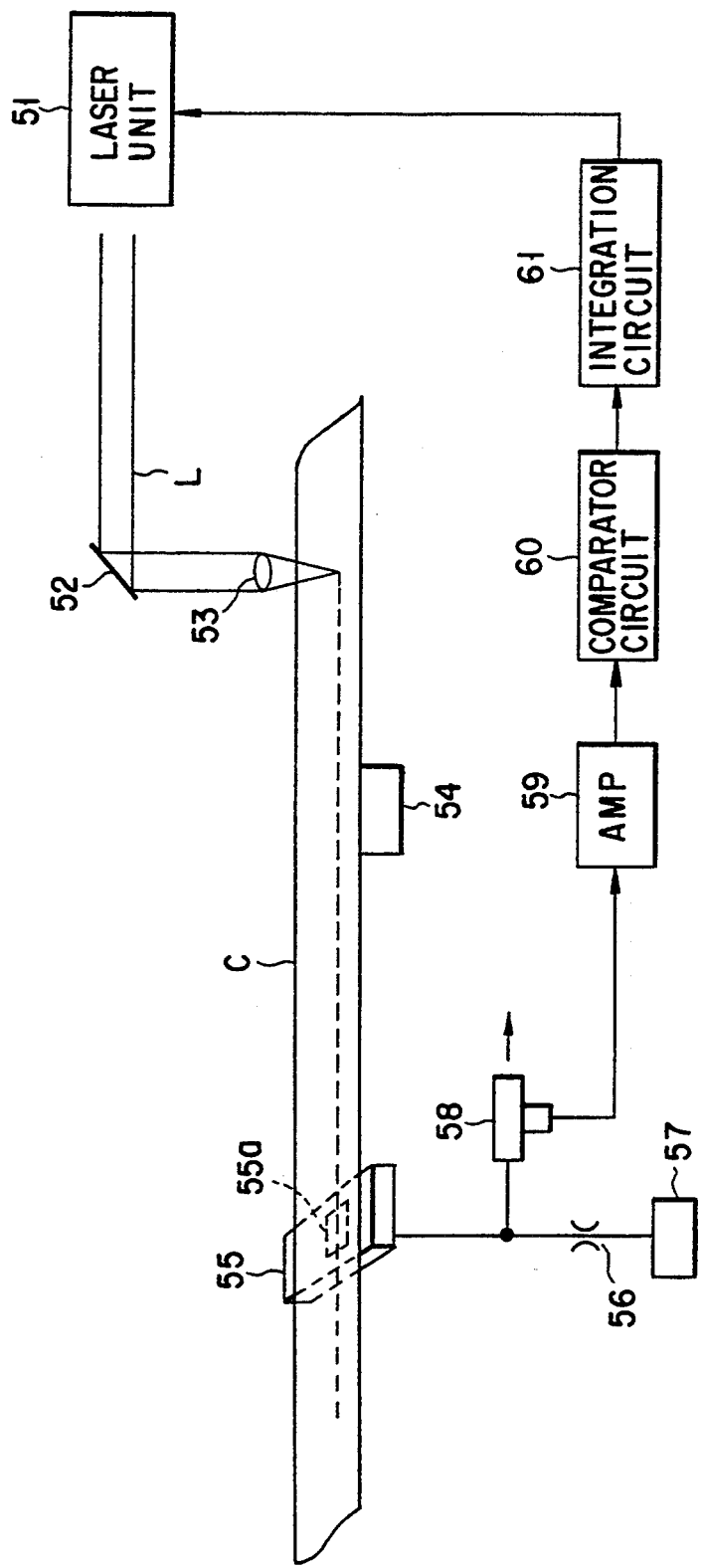
F I G. 1

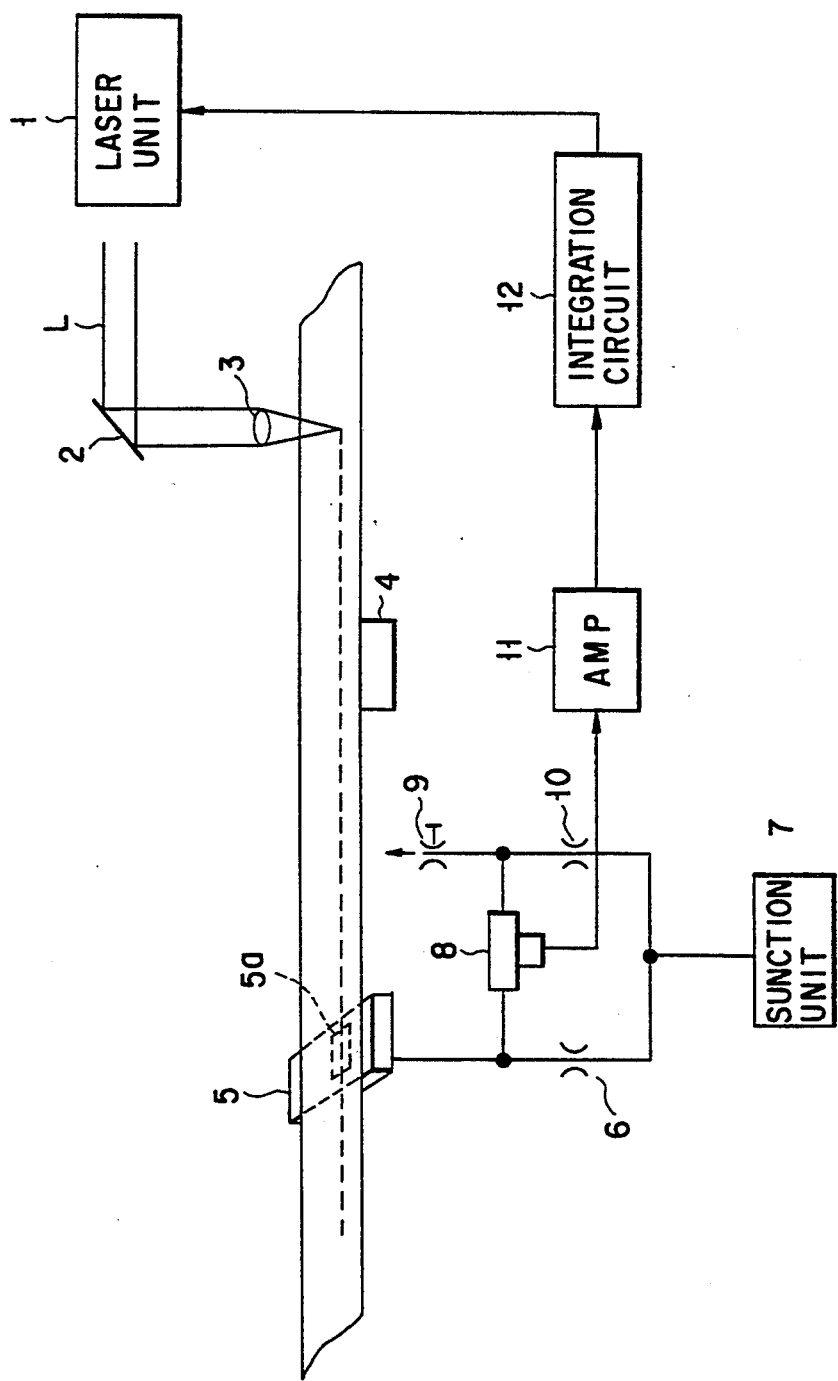
F I G. 2

AIR PERMEABILITY DETECTING METHOD AND APPARATUS FOR THE SAME

BACKGROUND OF THE INVENTION

1. Field of the Invention

The present invention relates to a method and apparatus for detecting the air permeability of vent holes formed in a belt-like sheet material and, more particularly, to an air permeability detecting method of comparing the permeating air resistance of vent holes set at a target air permeability with that of vent holes formed in the belt-like sheet material, and feeding back the difference as the comparison result to a laser unit, thereby controlling the intensity of a laser beam, and an apparatus for the same.

2. Description of the Related Art

Conventionally, as an apparatus for forming vent holes in a belt-like sheet material, a hole forming apparatus disclosed in Jpn. Pat. Appln. KOKAI Publication No. 63-188486 and the like are known. In this hole forming apparatus, a pulse laser beam is radiated to a mirror-surface pyramid, and a reflected laser beam is focused on a belt-like sheet material that moves in accordance with a predetermined radius of rotation, thereby forming fine holes in the belt-like sheet material.

As a method of detecting the porosity of the belt-like sheet material in which holes are formed by the above apparatus, a method of measuring the amount of light being transmitted through a hole portion and a method of measuring the amount of air permeating through the hole portion are known. Especially, as a method of measuring the porosity of chip paper used, for a example, in cigarettes, a method of measuring the permeating air amount is known.

Vent holes for diluting the inhalation concentrations of nicotine and tar are formed in the chip paper wound on the filter of a cigarette. The air permeability of the vent holes influences the taste of the cigarette. Therefore, it is important to control the air permeability at a predetermined value.

A conventional method of detecting the air permeability of the chip paper and an apparatus for the same will be described with reference to FIG. 1. As shown in FIG. 1, a pulse laser beam L oscillated by a laser unit 51 is reflected by a reflecting mirror 52 and focused by a condenser lens 53. The focused beam is radiated on chip paper C that moves at a predetermined speed. More specifically, the condenser lens 53 is adjusted such that the pulse laser beam L is focused on the chip paper C, thereby continuously forming holes in the moving chip paper C. The air permeability, as the porosity of the chip paper C, is determined in accordance with the conditions, e.g., the traveling speed of the chip paper C, the ON period, ON time, and intensity of the laser beam, and the material of the chip paper C.

As the chip paper C is moved, the vent holes formed in the chip paper C are moved at a predetermined speed in the longitudinal direction of the chip paper C. When the chip paper C passes above a dust collecting unit 54, dust from the chip paper C, generated during hole formation, is collected, and then the chip paper C passes above an air permeability detection unit 55. The air permeability detection unit 55 has a detection window 55a above which the chip paper C passes. A suction unit 57, for sucking the chip paper C on to the detection window 55a, is connected to the detection window 55a. An orifice 56 for converting an air flow rate to a pneumatic pressure is provided between the air permeability detection unit 55 and the suction unit 57. A differential pressure type converter 58 for converting a pressure difference between the pressure at the orifice 56 and the atmospheric pressure is provided between the air permeability detection unit 55 and the orifice 56.

The chip paper C is sucked, through the detection window 55a, by the suction pressure generated by the suction unit 57. At this time, the air permeability of the vent holes in the chip paper C, passing above the detection window 55a, is detected. More specifically, the flow rate of air drawn by the suction unit 57 is changed by a difference in air permeability. This flow rate is converted to a pneumatic pressure by the orifice 56. A change in pneumatic pressure is compared with the atmospheric pressure by the differential pressure type converter 58. The comparison result is converted to an electrical signal and detected as an air permeability.

The air permeability detected as the electrical signal in this manner is amplified by an amplifier 59 to a predetermined level and compared by a comparator circuit 60 with a preset target value, thereby obtaining a difference signal. The difference signal is supplied to an integration circuit 61 that stabilizes control, and is fed back as a control signal to the laser unit 51. As the permeating air amount of the vent holes of the chip paper C is changed, the oscillating laser intensity of the laser unit 51, to which the control signal is supplied, is changed.

The integration constant of the integration circuit 61 is set at an appropriate value considering the response time of the laser unit 51 and the traveling speed of the chip paper C.

In this manner, according to the conventional technique, variations in air permeability of the chip paper are detected as a change in pressure, a difference signal with respect to the atmospheric pressure as a reference is obtained, the difference signal is compared with a preset target value, and the comparison result is fed back to the laser unit, thereby controlling the laser oscillating intensity.

In this detecting method, however, the stability of the suction pressure at the suction unit for permeating air through the vent holes of the chip paper C is significant. More specifically, the suction pressure is changed depending on the material and air permeability of the chip paper C, variations in atmospheric pressure due to the weather and the like, the suction capability and stability of the suction fan, mechanical variations at other portions and the like. For example, when suction is performed at a pressure of 200 [mmAq], the suction pressure is changed by about 10 to 20 [mmAq] a day. Along with this change, the permeating air amount at the hole portion is also changed by about 3.4 [ml/mmAq] a day. When the suction pressure is changed by 10 [mmAq] a day, the permeating air amount is changed by about 34 [mml] a day. In this manner, if the suction pressure is not constant, it must be adjusted at least once a day.

When the suction pressure of the suction unit varies in this manner, the air permeability cannot be detected precisely, and the air permeability does not coincide with the target value. Even if the air permeability is stable, if the suction pressure varies due to the reasons described above, variations in suction pressure are detected as variations in air permeability. This detection signal is compared with the target value, and the comparison result is fed back to the laser unit. Therefore, the air permeability cannot be controlled correctly.

When the air permeability is not controlled correctly, the quality of product is degraded. Accordingly, an apparatus for always stabilizing the variations in suction pressure is required, not only increasing the entire size of the apparatus but also increasing the cost of the apparatus. In addition, it is very difficult to completely control the suction pressure to a predetermined value.

SUMMARY OF THE INVENTION

It is an object of the present invention to provide an air permeability detecting method which is not influenced by variations in suction pressure, and an apparatus for the same.

According to the present invention, there is provided an air permeability detecting apparatus for detecting an air permeability of a hole portion of a belt-like sheet material which is formed by a laser beam, comprising:

hole forming means for radiating a laser beam having a small spot diameter on the belt-like sheet material and for forming holes in the belt-like sheet material;

air permeability detecting means for detecting the air permeability of the hole portion, the air permeability detecting means having a first flow path for coupling a hole portion detection unit, above which a hole portion of the belt-like sheet material which is formed by the hole forming means passes, and a first orifice for converting a flow rate of air, drawn from the detection unit, to a pressure, a second flow path for coupling a valve, capable of adjusting a flow rate of passing air and having one end open to atmospheric air, and a second orifice for converting a flow rate of air drawn from the valve to a pressure, suction means, provided to outlet sides of the first and second orifices, for sucking the hole portion through the detection unit and drawing the atmospheric air through the valve, and pressure difference detecting means, connected between the first and second flow paths, for detecting a pressure difference between the pressure converted by the first orifice and the pressure converted by the second orifice, and converting the pressure difference to an electrical signal; and control means for feeding back a detection signal detected by the air permeability detecting means.

According to the present invention, there is also provided an air permeability detecting method of detecting an air permeability of a hole portion of a belt-like sheet material which is formed by a laser beam, comprising the steps of:

radiating a laser beam having a small spot diameter on the belt-like sheet material and forming holes in the belt-like sheet material;

causing air to flow in a hole portion by sucking the hole portion by the used of suction means; converting a flow rate of air to a pressure, causing air to flow by drawing air by the suction means through a valve whose diameter can be arbitrarily changed, and converting a flow rate of air to a pressure; and detecting a difference between the two pressures, converting the pressure difference to an electrical signal, and feeding back the electrical signal to a laser beam oscillating source, thereby controlling the oscillation intensity of the laser beam.

The operation of the present invention will be described based on its arrangement. The hole portion of the belt-like sheet material, which is formed by the laser beam, is caused to pass over the hole portion detection unit. The hole portion detection unit is connected to the suction unit through the first orifice, and the hole portion is sucked by the suction pressure of the suction unit. The flow rate of air obtained at this time is converted to a pressure by the first orifice and supplied to one terminal of the pressure difference detecting means.

The valve, which has one terminal open to the atmospheric air is connected to the suction unit through the second orifice, and is drawn by the suction pressure of the suction unit. The flow rate of air obtained at this time is converted to a pressure by the second orifice and supplied to the other terminal of the pressure difference detecting means.

The pressures from the two directions are supplied to the pressure difference detecting means, and a pressure difference between them is detected. This pressure difference is converted to an electrical signal and fed back to the hole forming means. If a control operation is performed such that this pressure difference is zero, the air permeability of the valve coincides with the air permeability of the hole portion.

Air is drawn from both the hole portion detection unit and the valve by the same suction unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 is a block diagram schematically showing a punching system, having a conventional air permeability detecting apparatus, for forming fine holes in a belt-like sheet;

FIG. 2 is a block diagram schematically showing a punching system, having an air permeability detecting apparatus of the present invention, for forming fine holes in a belt-like sheet.

DETAILED DESCRIPTION OF THE PREFERRED EMBODIMENTS

Figure 3:
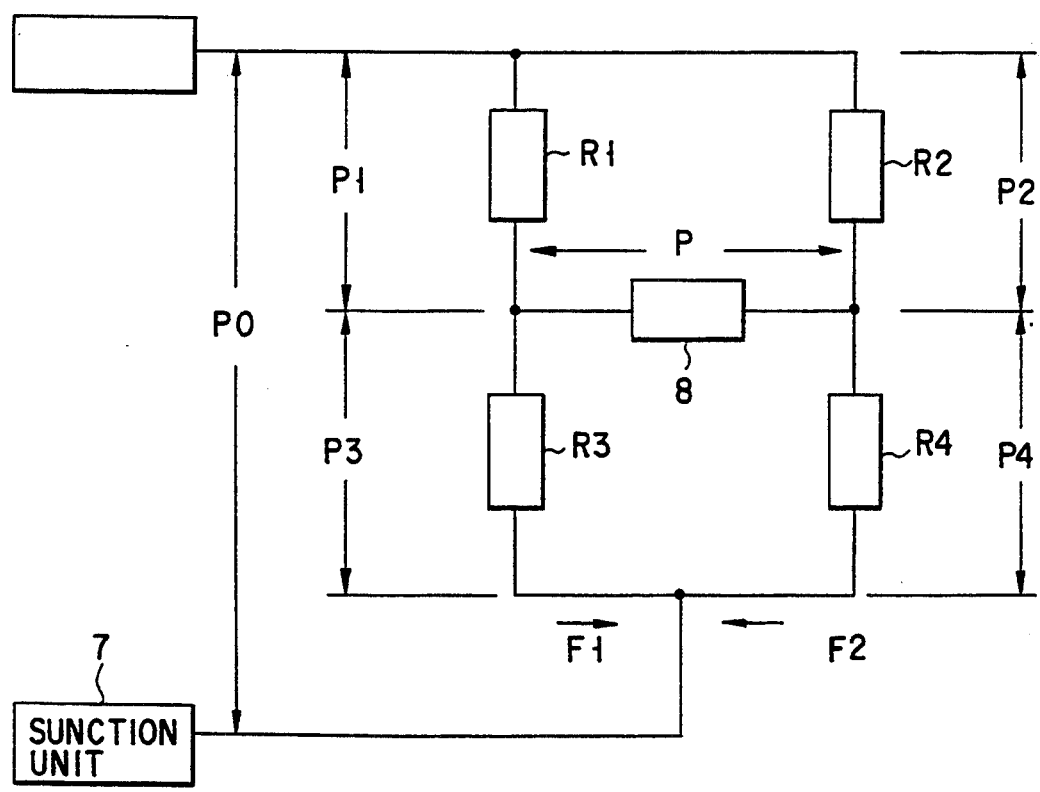
FIG. 3 is a block diagram for explaining a method of detecting the air permeability according to the present invention.

An air permeability detecting method according to a preferred embodiment of the present invention, and an apparatus for the same will be described with reference to the accompanying drawings.

FIG. 2 shows a punching system, having an air permeability detecting apparatus according to the present invention, for forming fine holes in a belt-like sheet. In the apparatus shown in FIG. 2, a pulse laser beam L, radiated by a laser unit 1 that performs pulse oscillation, is reflected by a reflecting mirror 2 and focused by a condenser lens 3. The focus beam is radiated on chip paper C that is moved at a predetermined speed. More specifically, the condenser lens 3 is adjusted such that the pulse laser beam L is focused on the chip paper C, and thus fine holes are continuously formed at focal points on the chip paper C along the moving direction. The chip paper C, having the fine holes formed therein in this manner, is moved at the predetermined speed in the longitudinal direction thereof. When the chip paper C passes above a dust collecting unit 4, dust of the chip paper C generated during hole formation is collected. Then, the chip paper C passes above an air permeability detection unit 5.

The air permeability detection unit 5 has a detection window 5a at a side thereof opposing the chip paper C, and a suction unit 7, for attracting the chip paper C to the detection window 5a, is connected to the detection window 5a. The suction pressure generated by the suction unit 7 sucks the chip paper C through the detection window 5a, and thus the air permeability of the vent holes in the chip paper C passing over the detection window 5a is detected. More specifically, the flow rate of air drawn by the suction unit 7 is changed due to a change in air permeability. This air flow rate is converted to a pressure by an orifice 6 provided between the air permeability detection unit 5 and the suction unit 7. This pressure is supplied to one terminal of a differential pressure type converter 8 provided between the air permeability detection unit 5 and the orifice 6.

A needle valve 9, in contact with the atmospheric air and capable of manually changing its permeating air amount, is connected to the suction unit 7, and is drawn by the suction pressure generated by the suction unit 7, simultaneously with the air permeability detection unit 5. The flow rate of air passing through the needle valve 9 by suction is converted to a pressure by an orifice 10 provided between the needle valve 9 and the suction unit 7, and is supplied to the other terminal of the differential pressure type converter 8 provided between the needle valve 9 and the orifice 10.

The differential pressure type converter 8 receives pressures from two directions, in this manner, a difference in pressure between the two directions is detected, and the pressure difference is converted to an electrical signal. The pressure difference which is converted to the electrical signal is amplified by an amplifier 11 to a predetermined level and supplied to an integration circuit 12. An integration signal obtained by the integration circuit 12 is fed back to the laser unit 1 as a control signal. Note that the integration constant of the integration circuit 12 is set to an appropriate value considering the response time of the laser unit 1 and the traveling speed of the chip paper C.

The orifices 6 and 10 are adjusted to have the same permeating air resistance, and the needle valve 9 is adjusted to have a desired air permeability. The air permeability of the vent holes is adjusted such that, when the air permeability detection unit 5 and the needle valve 9 are drawn by the suction unit 7, simultaneously, so that a difference in flow rate between air supplied from the vent holes in the chip paper C through the air permeability detection unit 5 and air supplied from the needle valve 9, is detected as a pressure difference by the differential pressure type converter 8; the pressure difference is always zero. More specifically, the oscillating intensity and the ON time of the laser beam generated by the laser unit 1 are adjusted, so that the air permeability of the vent holes always coincides with the air permeability of the needle valve 9.

The air permeability of the needle valve 9 is manually adjusted in such a manner that when a belt-like sheet sample having standard fine holes formed therein is supplied to the air permeability detection unit 5, a signal from the differential pressure type converter 8 becomes zero. Then, by this preliminary adjustment, the intensity of the laser beam generated by the laser unit 1 is automatically adjusted in accordance with the signal from the differential pressure type converter 8, and fine holes having the same size as that of the fine holes formed in the belt-like sheet sample are formed in the chip paper C.

The method of detecting the air permeability will be described in more detail with reference to FIG. 3.

Referring to FIG. 3, reference symbol R1 denotes the permeating air resistance of the air permeability detection unit 5 (hole portion of the chip paper); R2, the permeating air resistance of the needle valve 9; R3, the permeating air resistance of the orifice 6; R4, the permeating air resistance of the orifice 10; F1, the flow rate of air flowing via the permeating air resistances R1 and R3; F2, the flow rate F2 of air flowing via the permeating air resistances R2 and R4; P1, a pressure drop caused by the permeating air resistance R1; P2, a pressure drop caused by the permeating air resistance R2; P3, a pressure drop caused by the permeating air resistance R3; P4, a pressure drop caused by the permeating air resistance R4; P, a pressure difference generated across the two terminals of the differential pressure type converter 8; and P0, a suction pressure generated by the suction unit 7.

When the vent holes of the chip paper C pass above the air permeability detection unit 5, air is permeated through the vent holes of the chip paper C through the detection window 5a by the suction pressure generated by the suction unit 7. The flow rate of the permeated air is converted to a pressure by the orifice 6 and supplied to one terminal of the differential pressure type converter 8. The permeating air amount of the needle valve 9 which is drawn together simultaneously with the air permeability detection unit 5 by the suction unit 7 is set to a desired value. The flow rate of air permeated through the needle valve 9 is converted to a pressure by the orifice 10 and supplied to the other terminal of the differential pressure type converter 8.

When the permeating air resistance R3 of the orifice 6 is set equal to the permeating air resistance R4 of the orifice 10, if the target value of the permeating air resistance R2, set by the needle valve 9, coincides with the permeating air resistance R1 of the vent holes in the chip paper C actually measured from the air permeability detection unit 5 side; the pressure difference obtained by the differential pressure type converter 8 becomes zero. More specifically, the necessary condition for setting the pressure difference to zero, detected by the differential pressure type converter 8, is that the pressure drops P1 and P2 caused by the permeating air resistance R1 and R2, the equivalent resistors of which have one end each open to atmospheric air; are equal to each other, and that the pressure drop P3 caused by the permeating air resistance R3 and the pressure drop P4 caused by the permeating air resistance R4 are equal to each other.

That is, $P1 = P2$ and $P3 = P4$.

Regarding the product of the air flow amount and the permeating air resistance, the following equations are established:

$$F1 \times R1 = F2 \times R2$$

$$F1 \times R3 = F2 \times R4$$

A relation of $R1/R3 = R2/R4$ is established among the above four permeating air resistances.

The permeating air resistance R1 of the air permeability detection unit 5 is obtained from the above equations as follows:

$$R1 = R3(R2/R4)$$

Therefore, $$R1 = (R3/R4) \times R2 \quad (1)$$

is obtained.

When R3 and R4 are set equal in accordance with the above condition, $$R1 = R2$$

is obtained. Thus, when the pressure difference applied across the two terminals of the differential pressure type converter 8 is zero, the permeating air resistance of the air permeability detection unit 5 (the vent holes of the chip paper C) becomes equal to the permeating air resistance of the needle valve 9.

A case wherein a pressure difference occurs across the two terminals of the-differential pressure type converter 8 will be described.

When large holes are formed in the chip paper C to increase the air permeability and decrease the permeating air resistance R1 of the air permeability detection unit 5, the pressure drop P1, caused by the permeating air resistance R1, is decreased so that the pressure comes close to the atmospheric pressure, and a pressure difference of $P1 - P2 = -\Delta P$ is generated between the pressure drop P1 and the pressure drop P2 which is caused by the permeating air resistance R2 of the needle valve 9.

When small vent holes are formed in the chip paper C to decrease the air permeability and increase the permeating air resistance R1 of the air permeability detection unit 5, the pressure drop P1, caused by the permeating air resistance R1, is increased so that the pressure comes close to that of the suction pressure, and a pressure difference of $P1 - P2 = \Delta P$ is generated between the pressure drop P1 and the pressure drop P2 which is caused by the permeating air resistance R2 of the needle valve 9.

When the pressure difference is caused in this manner, a control signal corresponding to this pressure difference is fed back to the laser unit 1 to control it, such that the pressure difference is always zero. More specifically, when the laser unit 1 is controlled such that the pressure difference is set to zero, the air permeability of the chip paper C can always be maintained at a constant value (the air permeability of the needle valve 9).

The air permeability of the needle valve 9 may be adjusted to change the permeating air resistance, thereby adjusting the air permeability of the chip paper C. For example, to increase the air permeability of the chip paper C, the permeating air resistance of the needle valve 9 may be decreased.

As described above, when the laser unit 1 is controlled such that the pressure difference P across the two terminals of the differential pressure type converter 8 is always zero, the air permeability of the air permeability detection unit 5, i.e., the air permeability of the chip paper C coincides with the air permeability of the needle valve 9, and the air permeability of the chip paper C can be adjusted by adjusting the air permeability of the needle valve 9.

If the pressure difference p across the two terminals of the differential pressure type converter 8 is zero, the air permeability of the chip paper C, determined by the permeating air resistance R1, is not influenced by the variations in suction pressure, as is apparent from equation (1). More specifically, since the suction pressure for permeating air through the air permeability detection unit 5 and the suction pressure for permeating air through the needle valve 9 are generated, simultaneously, by the same suction unit 7, the influence of the variations in suction pressure P0 of the suction unit 7 is canceled.

Therefore, according to air permeability control of the air permeability detecting method of the present invention, the variations in air permeability due to the influence of the variations in suction pressure are eliminated. Unlike air permeability control according to the conventional air permeability detecting method, when the air permeability of the chip paper C is set at a correct value; it will not be controlled at an erroneous value.

When (R3/R4) in above equation (1) is considered as a proportional constant, R1 and R2 are proportional to each other. Since R1 is determined only by R2 in the same manner as in a case wherein $R3 = R4$, it is not influenced by the suction pressure. Therefore, the permeating air resistances of the orifices 6 and 10 need not necessarily be set to equal to each other, and can be set to any values to obtain accurate control.

As has been described above, according to the present invention, the influence caused by the variations in suction pressure, which is conventionally difficult to eliminate, can be eliminated simply by adding a needle valve and orifices to the conventional technique. As a result, the variations in permeating air amount, caused by the variations in suction pressure, can be suppressed at as low as about 0.125 [mml/mmAq], which is decreased to about 1/27 times that of the conventional technique. Accordingly, when the suction pressure is changed by 10 [mmAq], a change in air permeability is suppressed at about 1.25 [mml], and the suction pressure need be adjusted only about once every three days.

In addition, since an extra unit for stabilizing the suction pressure or a difference detection circuit is not needed, the size of the apparatus is not increased, and the cost of the apparatus itself is not increased.

According to the apparatus of the present invention, since the hole portion of the belt-like sheet material and the valve having a desired air permeability are drawn simultaneously by the suction means, a detection error in porosity caused by the variations over time in suction pressure is canceled, so that an air permeability detecting apparatus which is not influenced by the variations over time in suction pressure can be provided.

In addition, according to the apparatus of the present invention, since a large-size unit, e.g., a pressure difference detection circuit for comparing a target porosity and a detection result, is not needed, air permeability detection not influenced by the variations over time in suction pressure can be performed by an apparatus having a very simple arrangement, which is economical.

In addition, according to the method of the present invention, the porosity of the hole portion of the belt-like sheet material is detected and compared with a target value, and the comparison result is fed back to the hole forming means. Therefore, when the pressure of air drawn by suction from the valve and the pressure of air drawn by suction from the hole portion are always set equal to each other, holes having the same porosity as that of the valve are formed in the belt-like sheet material, thereby facilitating adjustment of the porosity of the chip paper C.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An air permeability detecting apparatus for detecting an air permeability of a hole portion of a belt-like sheet material which is formed by a laser beam, comprising:

hole forming means for radiating a light beam on the belt-like sheet material to form fine holes, means for detecting an amount of air passing through the fine holes, said detecting means including a base having a window above which the fine holes formed in the belt-like sheet material pass, adjusting means for allowing entrance of an external reference air flow and capable of adjusting the entrance of said reference air flow, suction means, coupled to the window of said base and said adjusting means, respectively, for sucking the belt-like sheet material onto the window in order to draw a detection air flow through the fine holes and for drawing said reference air flow through said adjusting means, and converting means for converting said reference air flow and said detection air flow to a reference pressure and a detection pressure, respectively;

detecting means for generating a difference detection electrical signal by detecting a pressure difference between said reference pressure and said detection pressure; and control means for controlling said hole forming means in response to a detection signal, thereby adjusting an optical intensity of said light beam.

2. An apparatus according to claim 1, wherein said hole forming means includes a laser for generating a pulse laser beam.

3. An apparatus according to claim 1, wherein said adjusting means includes a needle valve capable of manually adjusting a permeating air amount.

4. An apparatus according to claim 1, wherein said converting means includes an orifice.

5. An apparatus according to claim 1, wherein said control means includes an integrator for integrating a differential pressure electrical signal.

6. An air permeability detecting method for detecting an air permeability of a hole portion of a belt-like sheet material which is formed by a laser beam, comprising the steps of:

radiating a light beam on the belt-like sheet material to form fine holes;

sucking at the belt-like sheet material so as to cause a detection air flow to flow through the fine holes and converting said detection air flow to a detection pressure;

allowing an adjustable reference air flow to flow and converting said reference air flow to a reference pressure;

generating a differential pressure electrical signal by detecting a differential pressure between said detection pressure and said reference pressure; and controlling an optical intensity of said light beam radiated in response to said differential pressure electrical signal, thereby maintaining the fine holes formed in said belt-like sheet material at a predetermined air permeability.

7. A method according to claim 5, further comprising the step of; prior to forming the holes, determining said reference air flow at a predetermined value by using a sample in which predetermined fine holes are formed.

* * * * *